(12) United States Patent
Ringgenberg et al.

(10) Patent No.: US 12,296,673 B2
(45) Date of Patent: May 13, 2025

(54) METHOD AND SYSTEM OF DEPLOYING IGNITION INTERLOCK DEVICE FUNCTIONALITY

(71) Applicant: Consumer Safety Technology, LLC, Des Moines, IA (US)

(72) Inventors: Jennifer Ringgenberg, West Des Moines, IA (US); Mark Behl, Urbandale, IA (US); Thomas John Chess, Des Moines, IA (US)

(73) Assignee: Consumer Safety Technology, LLC, Des Moines, IA (US)

(*) Notice: Subject to any disclaimer, the term of this patent is extended or adjusted under 35 U.S.C. 154(b) by 43 days.

(21) Appl. No.: 18/101,671

(22) Filed: Jan. 26, 2023

(65) Prior Publication Data

US 2023/0249548 A1    Aug. 10, 2023

Related U.S. Application Data

(63) Continuation of application No. 15/931,883, filed on May 14, 2020, now Pat. No. 11,565,587.

(Continued)

(51) Int. Cl.
*B60K 28/06*    (2006.01)
*B60R 25/04*    (2013.01)
(Continued)

(52) U.S. Cl.
CPC ............ *B60K 28/063* (2013.01); *B60R 25/04* (2013.01); *G01N 33/4972* (2013.01);
(Continued)

(58) Field of Classification Search
CPC ............ B60K 28/063; B60K 2028/003; B60R 25/04; B60R 2025/0415; G01N 33/4972; G01N 33/98; B60W 2540/24; B60W 2540/043; G16H 50/20; G16H 50/70; A61B 5/0022; A61B 5/0077; A61B 5/082;
(Continued)

(56) References Cited

U.S. PATENT DOCUMENTS 3,824,538 A * 7/1974 Slemp ................. B60K 28/063
340/576
4,749,553 A * 6/1988 Lopez ................ G01N 33/4972
340/576

(Continued)

OTHER PUBLICATIONS

"5 Ways That SmartWeb Can Make Your Workload Easier," Smart Start Blog post published Dec. 17, 2019, at URL <https://www.smartstartinc.com/blog/5-ways-that-smartweb-can-make-your-workload-easier/> (9 pages).

(Continued)

*Primary Examiner* — Curtis J King
(74) *Attorney, Agent, or Firm* — Pauly, DeVries Smith & Deffner LLC

(57) ABSTRACT

A method and a system of deploying ignition interlock device functionality. The method comprises receiving data in authentication of a user account associated with the IID; rendering a user interface at the mobile computing device, the user interface including indication of a status of the user account associated with the IID; and receiving a selection of a user action responsive to the status of the user account associated with the IID.

20 Claims, 17 Drawing Sheets

Related U.S. Application Data

(60) Provisional application No. 62/848,502, filed on May 15, 2019.

(51) Int. Cl.
*G01N 33/497* (2006.01)
*B60K 28/00* (2006.01)

(52) U.S. Cl.
CPC . *B60K 2028/003* (2013.01); *B60R 2025/0415* (2013.01); *B60W 2540/24* (2013.01)

(58) Field of Classification Search
CPC ......... A61B 5/097; A61B 5/18; A61B 5/4023; A61B 5/4845; A61B 5/486; A61B 5/4863; A61B 5/7275; A61B 5/743; A61B 5/7445; A61B 2010/0009; A61B 2010/0087; A61B 2562/0219; G06F 19/00; G08B 21/02
See application file for complete search history.

(56) References Cited

U.S. PATENT DOCUMENTS

| | | | | |
|---|---|---|---|---|
| 5,020,628 | A * | 6/1991 | Bigliardi | G01N 33/4972 340/576 |
| 5,426,415 | A | 6/1995 | Prachar et al. | |
| 6,714,894 | B1 * | 3/2004 | Tobey | G06Q 40/00 702/182 |
| 6,748,792 | B1 * | 6/2004 | Freund | G07C 9/00563 340/426.2 |
| 7,934,577 | B2 | 5/2011 | DeVries et al. | |
| 8,336,665 | B1 * | 12/2012 | Saunders | B60K 28/063 340/576 |
| 8,560,010 | B2 * | 10/2013 | Koehn | B60K 28/063 455/556.1 |
| 8,844,337 | B2 * | 9/2014 | Kountotsis | G01N 33/50 73/23.3 |
| 8,899,748 | B1 * | 12/2014 | Migdal | A61B 5/004 351/210 |
| 8,957,771 | B2 | 2/2015 | Arringdale et al. | |
| 9,241,054 | B1 * | 1/2016 | Roberts | G01N 33/4972 |
| 9,272,713 | B1 * | 3/2016 | Dvoskin | B60W 40/08 |
| 9,442,103 | B1 * | 9/2016 | Goad | G01N 33/4972 |
| 9,643,186 | B1 * | 5/2017 | Ahmad | G01N 33/542 |
| 9,707,845 | B1 * | 7/2017 | Nienhouse | B60K 28/063 |
| 9,811,997 | B2 * | 11/2017 | Stearns | G08B 21/02 |
| 10,421,358 | B1 * | 9/2019 | Marrisette, Sr. | B60K 28/02 |
| 10,984,480 | B1 * | 4/2021 | Srey | G06Q 40/08 |
| 11,565,587 | B2 | 1/2023 | Ringgenberg et al. | |
| 11,971,395 | B2 * | 4/2024 | DeVries | G01N 33/4972 |
| 2002/0008644 | A1 * | 1/2002 | Flick | B60R 25/33 340/988 |
| 2002/0014977 | A1 * | 2/2002 | Flick | B60R 25/33 340/988 |
| 2002/0014978 | A1 * | 2/2002 | Flick | B60R 25/04 340/988 |
| 2002/0021242 | A1 * | 2/2002 | Flick | G08G 1/127 342/357.395 |
| 2002/0158777 | A1 * | 10/2002 | Flick | B60R 25/104 340/988 |
| 2005/0053523 | A1 * | 3/2005 | Brooke | G01N 33/4972 422/68.1 |
| 2005/0137755 | A1 * | 6/2005 | Chase | G07C 5/085 701/1 |
| 2005/0190080 | A1 | 9/2005 | Flick | |
| 2006/0179901 | A1 * | 8/2006 | Schlitt | B60R 25/0225 70/209 |
| 2007/0107728 | A1 * | 5/2007 | Ricciardelli | A61B 5/083 128/204.22 |
| 2009/0060287 | A1 * | 3/2009 | Hyde | A61B 5/7435 382/118 |
| 2009/0111486 | A1 * | 4/2009 | Burstrom | H04M 1/7243 455/456.3 |
| 2009/0164141 | A1 * | 6/2009 | Lee | G01N 33/4972 73/23.3 |
| 2009/0187111 | A1 * | 7/2009 | Reilly, Jr. | A61B 5/097 422/84 |
| 2010/0036592 | A1 * | 2/2010 | Osaki | B60T 7/14 701/113 |
| 2010/0152976 | A1 * | 6/2010 | White | A61B 5/14546 700/79 |
| 2010/0294583 | A1 * | 11/2010 | Biondo | A61B 5/082 340/576 |
| 2011/0079073 | A1 * | 4/2011 | Keays | G01N 33/4972 73/23.3 |
| 2011/0084820 | A1 | 4/2011 | Walter et al. | |
| 2011/0266160 | A1 * | 11/2011 | Campbell | G01N 33/49 205/785.5 |
| 2011/0291827 | A1 * | 12/2011 | Baldocchi | G08B 21/0476 340/539.11 |
| 2011/0304465 | A1 * | 12/2011 | Boult | B60K 28/06 340/576 |
| 2012/0031165 | A1 * | 2/2012 | Ruocco | A61B 5/097 73/23.3 |
| 2012/0234708 | A1 * | 9/2012 | Chabot | B60R 11/02 206/320 |
| 2012/0323770 | A1 * | 12/2012 | Michael | G08G 1/054 705/39 |
| 2013/0021153 | A1 * | 1/2013 | Keays | G06Q 50/265 340/539.12 |
| 2013/0297387 | A1 * | 11/2013 | Michael | G06Q 30/02 705/13 |
| 2014/0003676 | A1 * | 1/2014 | Baughman | A61B 5/157 382/124 |
| 2014/0164233 | A1 | 6/2014 | Comeau et al. | |
| 2014/0165697 | A1 | 6/2014 | Mochizuki et al. | |
| 2014/0165698 | A1 | 6/2014 | Mochizuki et al. | |
| 2014/0215883 | A1 * | 8/2014 | Milde, Jr. | G07C 9/00896 42/70.11 |
| 2014/0335905 | A1 * | 11/2014 | Bhoot | H04W 4/02 73/23.3 |
| 2014/0365142 | A1 * | 12/2014 | Baldwin | A61B 5/0002 702/24 |
| 2015/0084774 | A1 * | 3/2015 | Wojcik | G01N 33/4972 340/573.1 |
| 2015/0355162 | A1 * | 12/2015 | Leach | G01N 33/4972 73/23.3 |
| 2015/0356519 | A1 * | 12/2015 | Wansley | G06Q 30/0267 705/7.21 |
| 2016/0082837 | A1 | 3/2016 | Comeau et al. | |
| 2016/0196737 | A1 * | 7/2016 | Martin | G08B 25/10 340/539.13 |
| 2016/0349239 | A1 * | 12/2016 | Chien | G01N 33/4972 |
| 2017/0095040 | A1 * | 4/2017 | Byrd | A44B 15/005 |
| 2017/0101006 | A1 * | 4/2017 | DeVries | A61B 5/4845 |
| 2017/0101007 | A1 | 4/2017 | DeVries et al. | |
| 2017/0176411 | A1 * | 6/2017 | Trainor | B60K 28/063 |
| 2017/0326978 | A1 * | 11/2017 | Nienhouse | H04Q 9/00 |
| 2018/0022353 | A1 * | 1/2018 | Thompson | F16D 41/00 701/22 |
| 2018/0091930 | A1 | 3/2018 | Jefferies | |
| 2018/0101721 | A1 * | 4/2018 | Nienhouse | B60K 28/063 |
| 2018/0125420 | A1 | 5/2018 | Keays et al. | |
| 2018/0177684 | A1 * | 6/2018 | Deacon | G16H 40/67 |
| 2018/0182258 | A1 * | 6/2018 | Deacon | G09B 5/02 |
| 2018/0182497 | A1 * | 6/2018 | Deacon | G16H 20/13 |
| 2018/0306776 | A1 * | 10/2018 | Cado | G01N 33/4972 |
| 2018/0351557 | A1 * | 12/2018 | Jim | G06F 30/327 |
| 2019/0141463 | A1 * | 5/2019 | Cabouli | H04R 27/00 |
| 2019/0308556 | A1 * | 10/2019 | Hu | B60Q 11/005 |
| 2019/0311101 | A1 * | 10/2019 | Nienhouse | A61B 5/1176 |
| 2020/0124589 | A1 * | 4/2020 | Gonzales | G07C 9/00309 |
| 2020/0152080 | A1 * | 5/2020 | Wu | G06Q 30/0631 |
| 2020/0171944 | A1 * | 6/2020 | Hanna | B60W 50/0098 |
| 2020/0256848 | A1 * | 8/2020 | Keays | A61B 5/4845 |
| 2020/0361314 | A1 | 11/2020 | Ringgenberg et al. | |
| 2021/0073529 | A1 * | 3/2021 | Thompson | G06V 20/56 |
| 2021/0222660 | A1 * | 7/2021 | Gil Vera | F02N 11/087 |
| 2021/0394764 | A1 * | 12/2021 | Clines | G06F 21/35 |
| 2022/0065844 | A1 * | 3/2022 | Keays | G01N 33/4972 |

(56) References Cited

U.S. PATENT DOCUMENTS

| | | | | |
|---|---|---|---|---|
| 2022/0073079 | A1* | 3/2022 | Nilsson | G06V 10/764 |
| 2023/0184742 | A1* | 6/2023 | Keays | G08B 5/36 |
| | | | | 340/870.07 |
| 2023/0210456 | A1* | 7/2023 | Nothacker | G16H 50/30 |
| | | | | 340/573.1 |
| 2023/0286379 | A1* | 9/2023 | Steel | A61B 5/163 |
| 2023/0331160 | A1* | 10/2023 | Diessner | B60D 1/36 |
| 2023/0401883 | A1* | 12/2023 | Thompson | G08G 1/096791 |

OTHER PUBLICATIONS

"Alcohol Monitoring-Scram LinkedIn SlideShare and Presentation," NCSCCLE & NCAJ DUI DWI Masters—Continuing Legal Education, Sep. 21, 2015, 104 pages.

"ECBA Lunch-n-Learn Smart Start Nuts & Bolts Event Details and Presentation," Erie County Bar Association, Feb. 26, 2019, 51 pages.

"Four Powerful Advantages of Smart Start's Client Portal," Smart Start Client Portal Information published Nov. 21, 2019, at URL <https://www.smartstartinc.com/blog/four-powerful-advantages-of-smart-starts-client-portal/> (6 pages).

"Mobile Alcohol Monitoring Makes SmartWeb Valuable," Smart Start Blog post published Apr. 1, 2020, at URL <https://www.smartstartinc.com/blog/mobile-alcohol-monitoring-makes-smartweb-valuable/> (8 pages).

"Non-Final Office Action," for U.S. Appl. No. 15/931,883 mailed Apr. 5, 2022 (16 pages).

"Notice of Allowance," for U.S. Appl. No. 15/931,883 mailed Sep. 29, 2022 (13 pages).

"Part 2: Getting Started with the Smart Start Client Portal," Smart Start Client Portal Information published Apr. 17, 2019, at URL <https://www.smartstartinc.com/blog/getting-started-smart-start-client-portal/> (6 pages).

"Part 3: Making Smart Start Payments and Auto-Pay on the Client Portal," Smart Start Client Portal Information published on Apr. 24, 2019, at URL <https://www.smartstartinc.com/blog/making-payments-auto-pay-client-portal/> (8 pages).

"Part 4: Big Reasons Why Smart Start's Client Portal Helps You," Smart Start Client Portal Information published Apr. 29, 2019, at URL <https://www.smartstartinc.com/blog/how-smart-start-client-portal-helps-clients/> (7 pages).

"Part 5: Ignition Interlock Lockout Codes and More on the Client Portal," Smart Start Client Portal Information published May 3, 2019, at URL<https://www.smartstartinc.com/blog/ignition-interlock-lockout-codes-the-client-portal/> (6 pages).

"Screenshots From Online Portal System for Users of Intoxalock Ignition Interlock Devices, captured Jan. 2018".

"Smart Start Client Portal Page," Smart Start Client Portal Web page accessed Jun. 10, 2020, at URL<https://www.smartstartinc.com/client-portal/> (11 pages).

"Smart Start Client Portal," App Listing in Google Play Store updated May 20, 2020, found at URL <https://play.google.com/store/apps/details?id-com.smartstartinc.clientportal.US&hl=en_US> (4 pages).

"Smart Start's Client Portal Helps Clients Manage Their Bottom Line," Smart Start blog post published Jan. 22, 2020, at URL <https://www.smartstartinc.com/blog/smart-starts-client-portal-helps-manage-their-bottom-line/> (7 pages).

* cited by examiner

1700

Receiving data in authentication of a user account associated with the IID
1710

Rendering a user interface at the mobile computing device, the user interface including indication of a status of the user account associated with the IID
1720

Receiving a selection of a user action responsive to the status of the user account associated with the IID
1730

FIG. 17

METHOD AND SYSTEM OF DEPLOYING IGNITION INTERLOCK DEVICE FUNCTIONALITY

This application is a continuation of U.S. patent application Ser. No. 15/931,883, filed May 14, 2020, which claims the benefit of U.S. Provisional Application No. 62/848,502, filed May 15, 2019, the contents of which are herein incorporated by reference.

TECHNICAL FIELD

The present disclosure generally relates to deployment of ignition interlock devices and associated interfaces.

BACKGROUND

Vehicles can incorporate a breath alcohol ignition interlock devices (IID) to prevent a driver from operating a vehicle while intoxicated with alcohol. Such devices are designed to prevent a driver from starting a motor vehicle when the driver's breath alcohol concentration (BAC) is at or above a set alcohol concentration threshold. Each state in the U.S. has adopted a law providing for use of such IID devices as a sanction for drivers convicted of driving while intoxicated, or as a condition of restoring some driving privileges after such offenses.

In operation, a driver must use a IID device by blowing into a mouthpiece portion of the IID coupled to an alcohol-sensing element such as a fuel cell that measures the amount of alcohol in the driver's breath, thereby providing a reliable estimate of the blood alcohol concentration in the driver's blood. The IID reads a signal generated from the fuel cell or similar alcohol-sensing element, and determines whether the driver's breath alcohol content exceeds a threshold amount. If the driver's blood alcohol content does not exceed the threshold, the driver is determined not to be intoxicated and the IID allows the vehicle to start and run by electrically enabling a system within the vehicle, such as the starter, fuel pump, or ignition system. If the breath sample delivered from the driver to IID registers a higher breath alcohol content than the predetermined allowable threshold, the vehicle is disabled from starting, and the IID device records a violation.

BRIEF DESCRIPTION OF THE DRAWINGS

FIG. 17 illustrates, in an example embodiment, a method of deploying ignition interlock device functionality.

DETAILED DESCRIPTION

Figure 1:
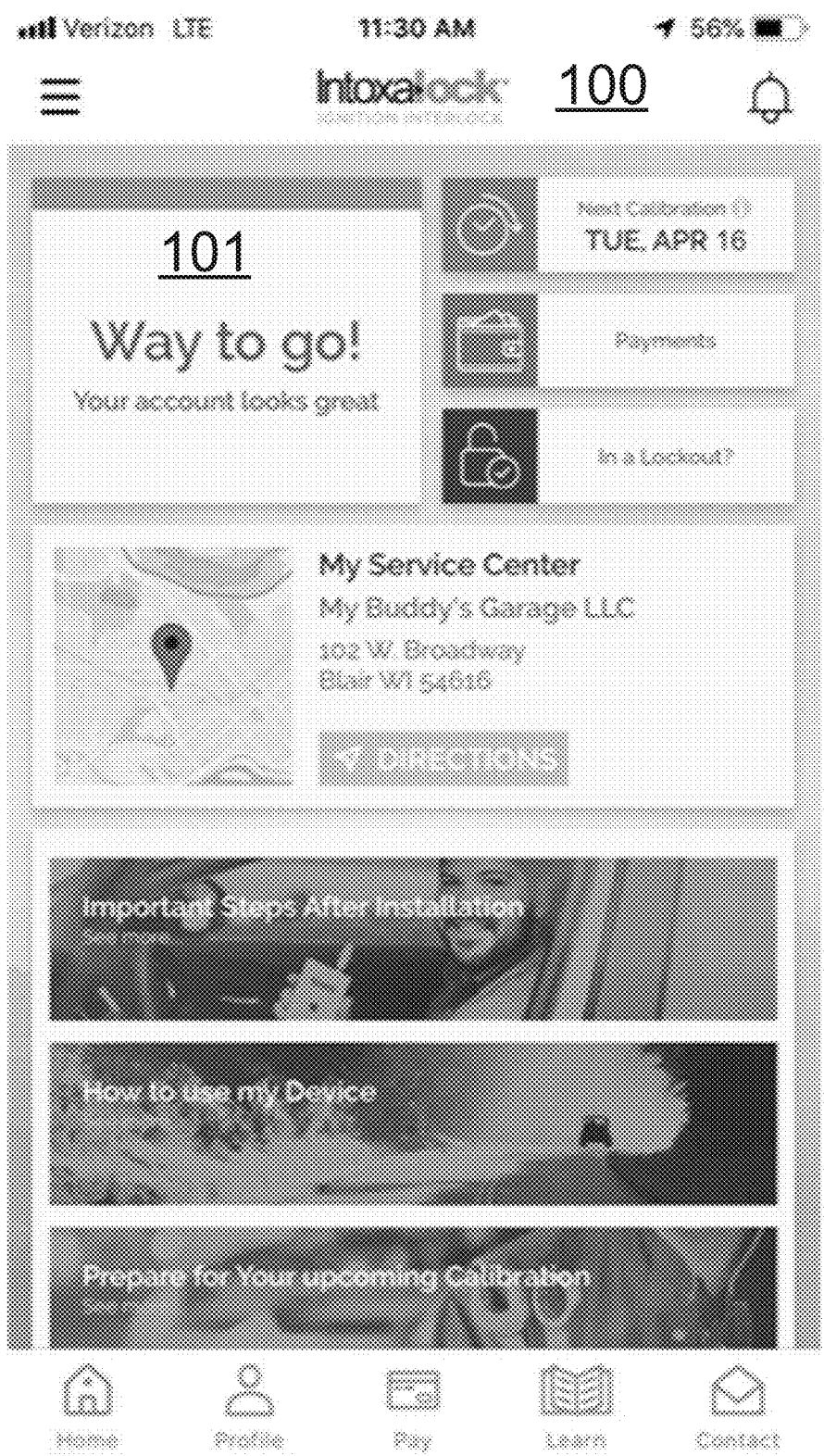
FIG. 1 is a home page of a mobile application for a customer of an intoxication interlock device in accordance with various embodiments herein.

Among other benefits and technical effects, embodiments provided herein provide mobile application functionality by way of a responsive interface for managing comprehensive IID system and service aspects, in a manner customized for each individual user. A mobile application as described herein provides an automated, efficient and responsive communication mechanism between the driver customer and the IID system provider, including with a third party service center or similar resource entity. In accordance with user interface configurations disclosed herein, an IID user can fulfill IID system requirements as they arise in real time, such as (but not limited to) interacting in real time with vehicle lockout conditions, review IID device and system tutorials, sign a lease contract, schedule IID device calibration upon demand, report vehicle maintenance, check account or profile related statements and make payments, among other IID system aspects.

The interlock provider company can be a source of important and valuable information to the user, including user manuals, trouble shooting device, state regulation information, and device information. Because the IID is connected to the customer's vehicle, the interlock provider company has information about the customer's device that may be useful and valuable to the customer. The terms "user" and "customer" are used interchangeably herein.

A typical IID device meets guidelines established by the National Highway Traffic Safety Administration (NHTSA) in published model specifications for IIDs, which specify various tests that such a device must pass to make it an effective and reliable deterrent to intoxicated driving. For example, the model specifies tests designed to ensure a specified minimum volume of breath is delivered at a specified minimum flow rate against less than a specified maximum back pressure to ensure that an accurate result is produced, and specifies how such a device should be installed into a vehicle to prevent the vehicle from operating pending a determination that the driver is not intoxicated. The model also requires that a device pass a re-calibration test within a specified tolerance for at least seven days past its mandated recalibration period, which can vary from 30 to 90 days.

Embodiments herein recognize that there usually arises need for an IID user to communicate in real time with the interlock provider system or company that provides the IID service to the user. Examples of needs for communication include payments, performing required calibrations, performing required periodic downloads of information from the IID, and performing lockout resets of the device if a user is locked out after an alcohol sample exceeds the alcohol threshold.

In operation, repeated use of the IID device can contaminate the fuel cell or other alcohol sensing element, causing its sensitivity to ethanol in the user's breath to drift and vary over time. To ensure that the IID measures alcohol accurately and consistently, regulations require that the IID be recalibrated from time to time, and that the IID be able to provide consistent results during and shortly after a stated recalibration interval.

Recalibration typically involves recalibrating the IID device, or at least the portion of the IID device containing the fuel cell, installed in the vehicle or replacing it with another recently-calibrated IID device. If the IID is replaced, the removed device can be sent back to the manufacturer's calibration facility for recalibration, after which it is sent back to an installation or service center to be returned to service in another vehicle. Alternatively, the IID is recalibrated at a service center that is geographically close to the customer in some embodiments. The recalibration process involves using a reference gas having a known concentration of ethanol, such as compressed gas from a tank or gas generated using a wet bath solution. The reference gas is provided to the fuel cell or other alcohol sensing element, and the indicated output of the device is adjusted to correspond to the known ethanol concentration of the reference gas.

Provided is a method of deploying ignition interlock device functionality. The method, executed in a processor of a mobile computing and communication device in one embodiment, comprises receiving data in authentication of a user account associated with the IID; rendering a user interface at the mobile computing device, the user interface including indication of a status of the user account associated with the IID; and receiving a selection of a user action responsive to the status of the user account associated with the IID.

Also provided is a mobile computing system, which in embodiments can be a handheld or tablet based computing system, for deploying ignition interlock device functionality. The system includes a processor and a memory storing executable code or instructions. The instructions, when executed in the processor, causing operations comprising receiving data in authentication of a user account associated with the IID; rendering a user interface at the mobile computing device, the user interface including indication of a status of the user account associated with the IID; and receiving a selection of a user action responsive to the status of the user account associated with the IID.

Further provided is a non-transitory memory medium storing executable instructions. The instructions, when executed in one or more processors, causing operations comprising receiving data in authentication of a user account associated with the IID; rendering a user interface at the mobile computing device, the user interface including indication of a status of the user account associated with the IID; and receiving a selection of a user action responsive to the status of the user account associated with the IID.

FIG. 1 is a home page 100 rendered via a mobile application for a customer or user of an intoxication interlock device in accordance with various embodiments. When a user logs into the mobile application, an icon can be displayed, providing a status indicator 101 whether the user needs to take action. For example, the status indicator 101 could communicate that the user is behind in a payment. The system can also access many different sources of data that would be helpful to the user. Examples of data include device data, environmental conditions, a database of state rules regarding IID usage, the interlock company's historical records of customer behavior and outcomes in aggregate, and the interlock company's integration with state systems. Using these data sources, the interlock company can provide valuable information, including advice to tell users how to progress towards getting their vehicle operation license privileges back. Status indicator 101 can also be referred to as an action card. For example, an interlock company will be able to warn a user that they are at risk of having their terms extended in compliance removal programs. The system could provide an extension risk score (High, Medium, Low) of terms are likely to be extended based on user behavior and what has happened to other users.

Figure 2:
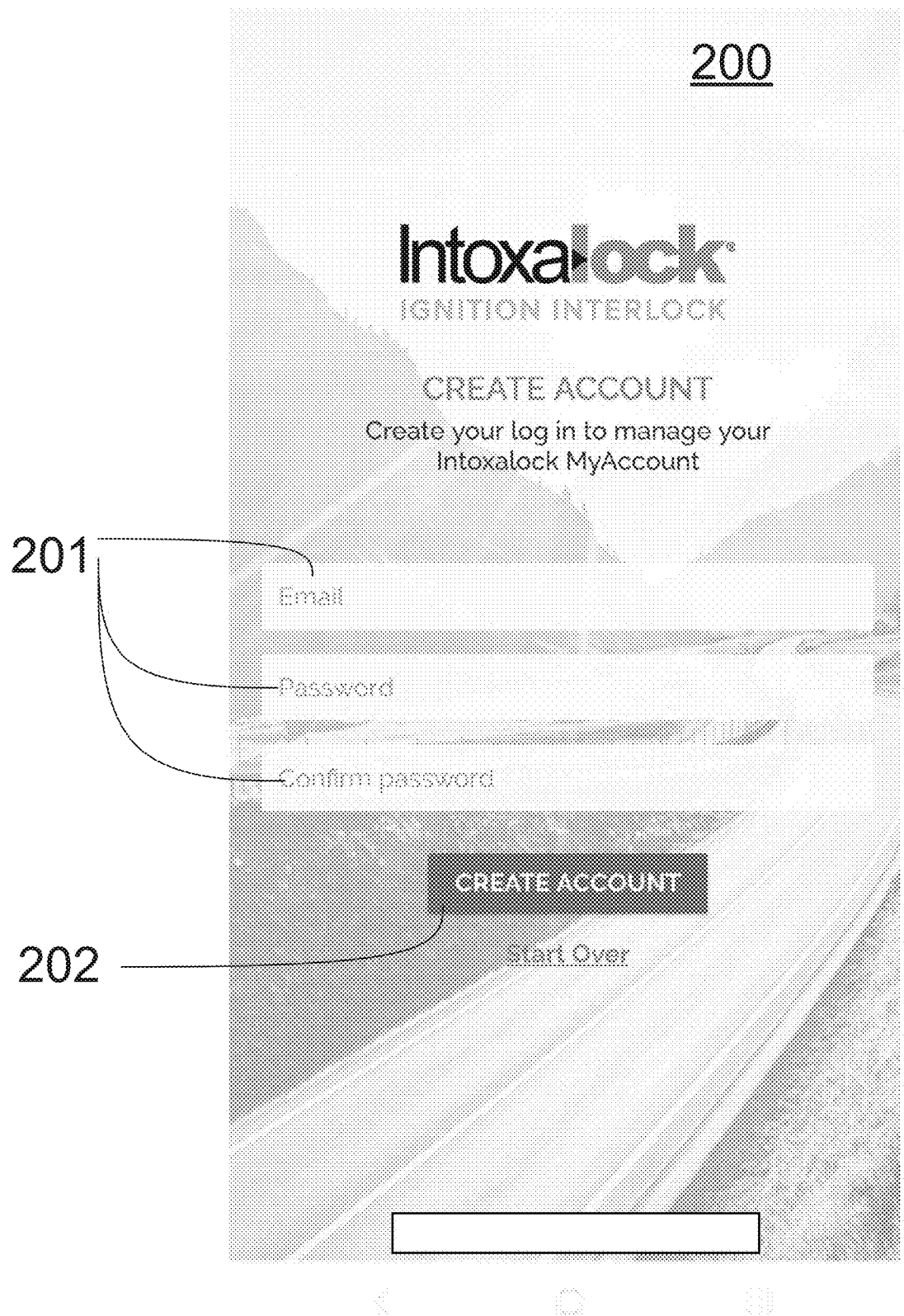
FIG. 2 is an account creation page of the mobile application of FIG. 1 in accordance with various embodiments herein.

FIG. 2 is an account creation page 200 of the mobile application of FIG. 1 in accordance with various embodiments. A user can provide, upon account creation, personal information including communication information 201 and related personal details for registering an IID related account 202, in some embodiments associated with a particular identified vehicle.

Figure 3:
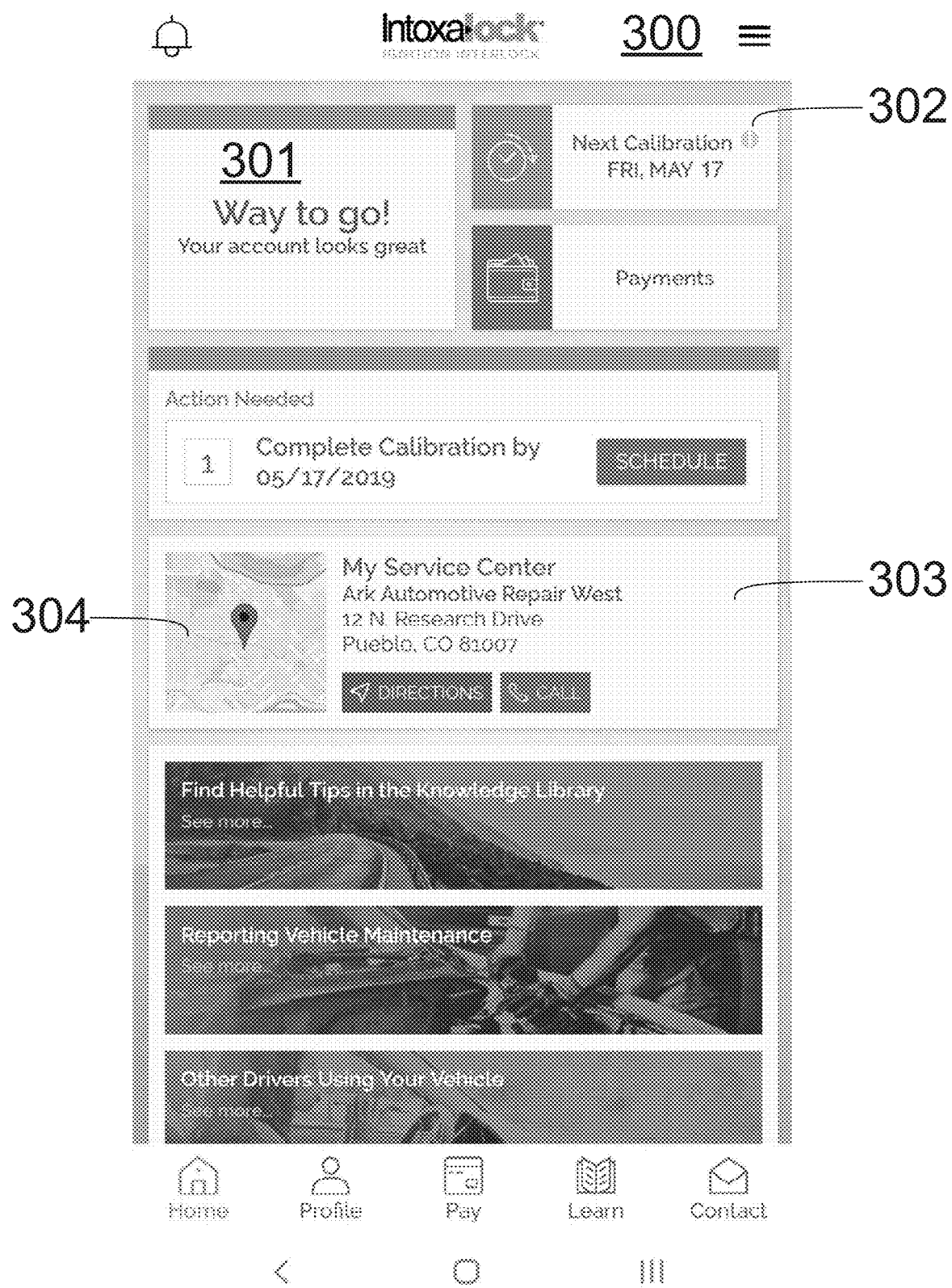
FIG. 3 is another home page of the mobile application of FIG. 1 in accordance with various embodiments herein.

FIG. 3 is another home page 300 of the mobile application of FIG. 1 in accordance with various embodiments, including status indicator 301. A re-calibration due date 302 for the IID installed in the user's vehicle can be displayed. A geographical location that identifies a closest location re-calibration service facility 303 can be shown to a user, optionally with a map display 304 basin accordance with GPS location functionality of the mobile device and IID system.

Figure 4:
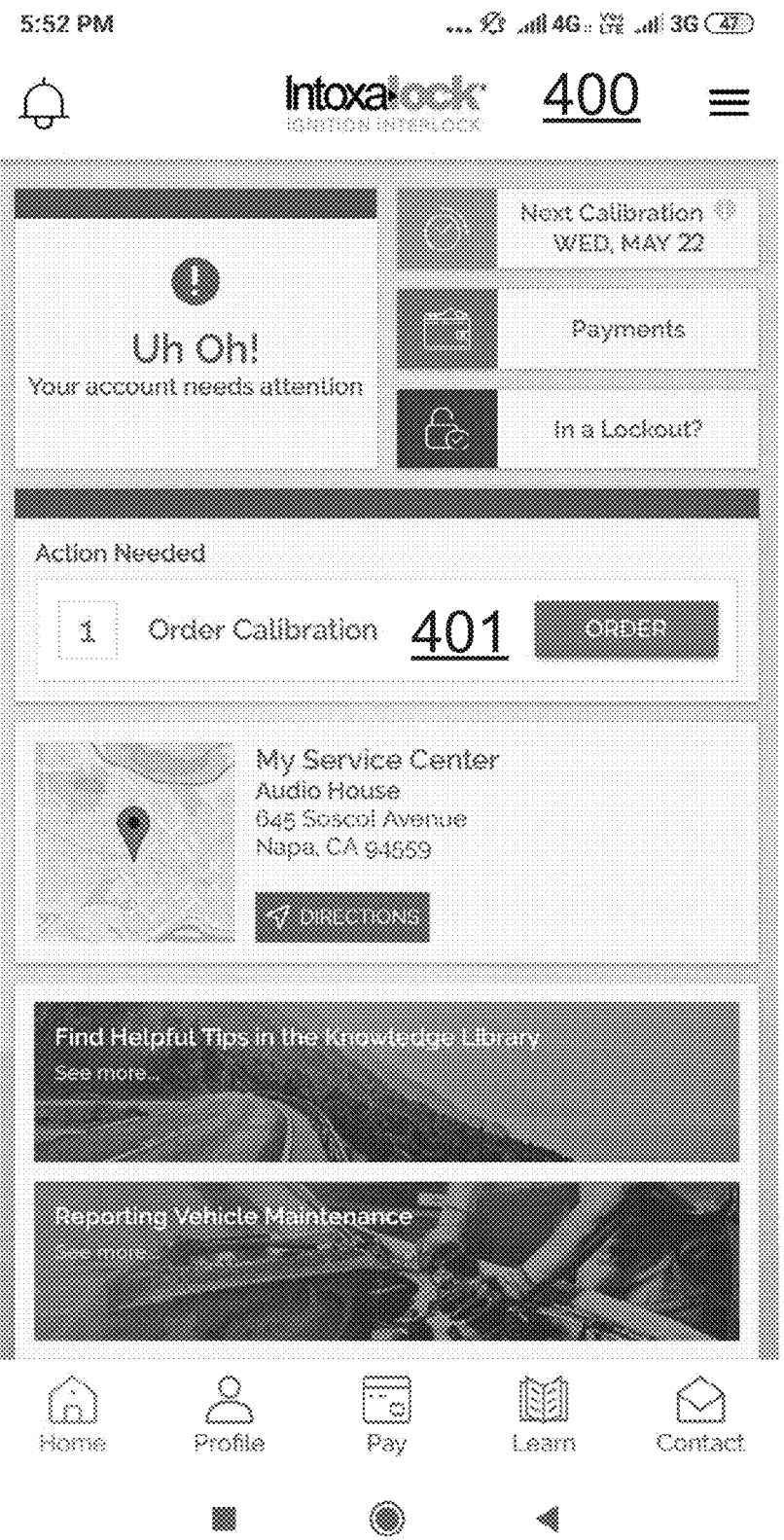
FIG. 4 is another home page of the mobile application of FIG. 1 in accordance with various embodiments herein.

FIG. 4 is another home page 400 of the mobile application of FIG. 1 in accordance with various embodiments. Among other aspects, the user is able to schedule an appointment with the service facility identified in FIG. 3 using a selection interface icon presented within user interface display home page 400.

Figure 5:
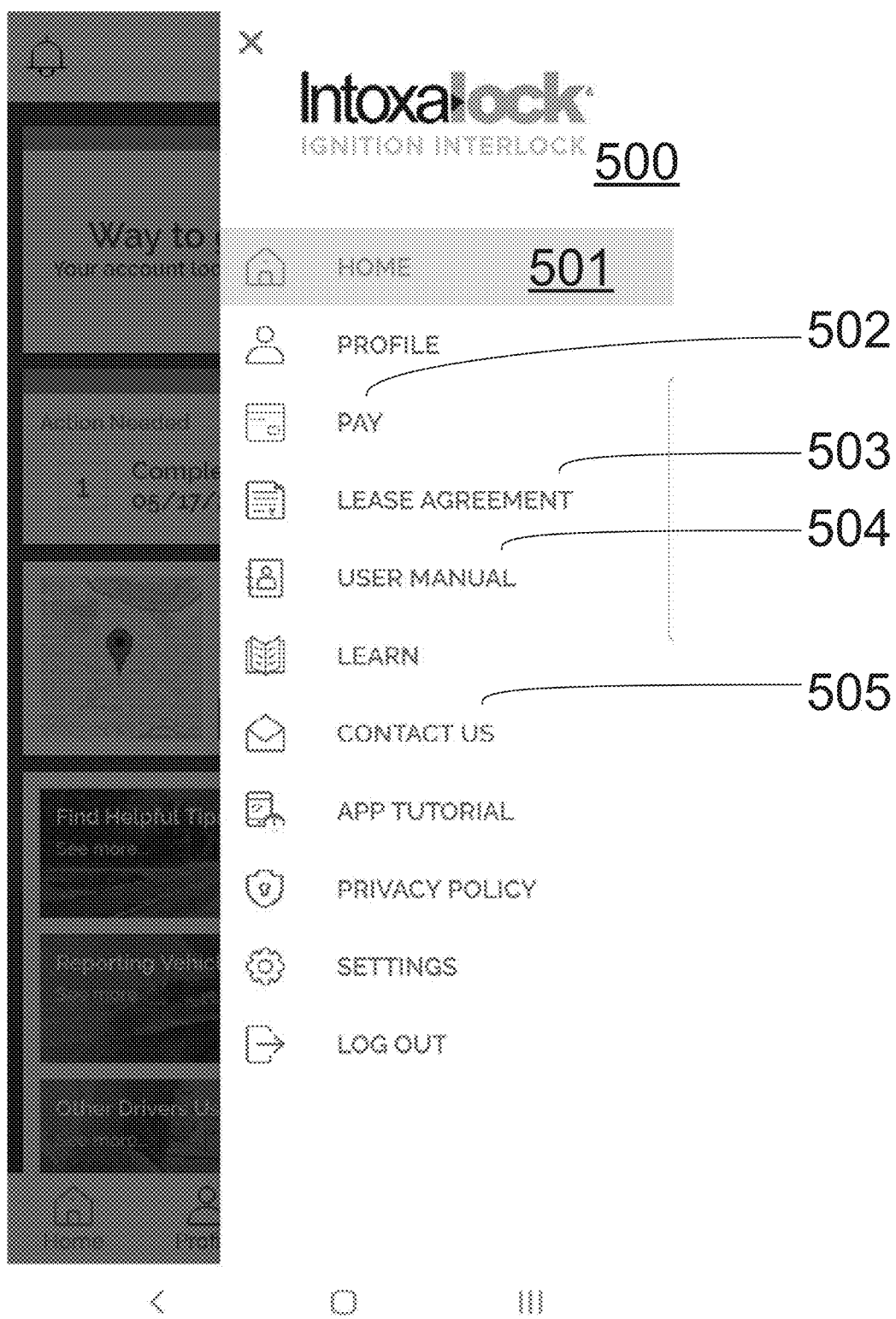
FIG. 5 is a navigation menu of the mobile application of FIG. 1 in accordance with various embodiments herein.

FIG. 5 is a navigation menu 500 of the mobile application of FIG. 1 in accordance with various embodiments. Among other aspects presented, a home listing 501 provides selectable options accessing digital facilities including payment facility 502, an IID lease agreement record 503 associated with the user account, an IID user manual 504, and options for initiating communication with the IID provider in real time.

Figure 6:
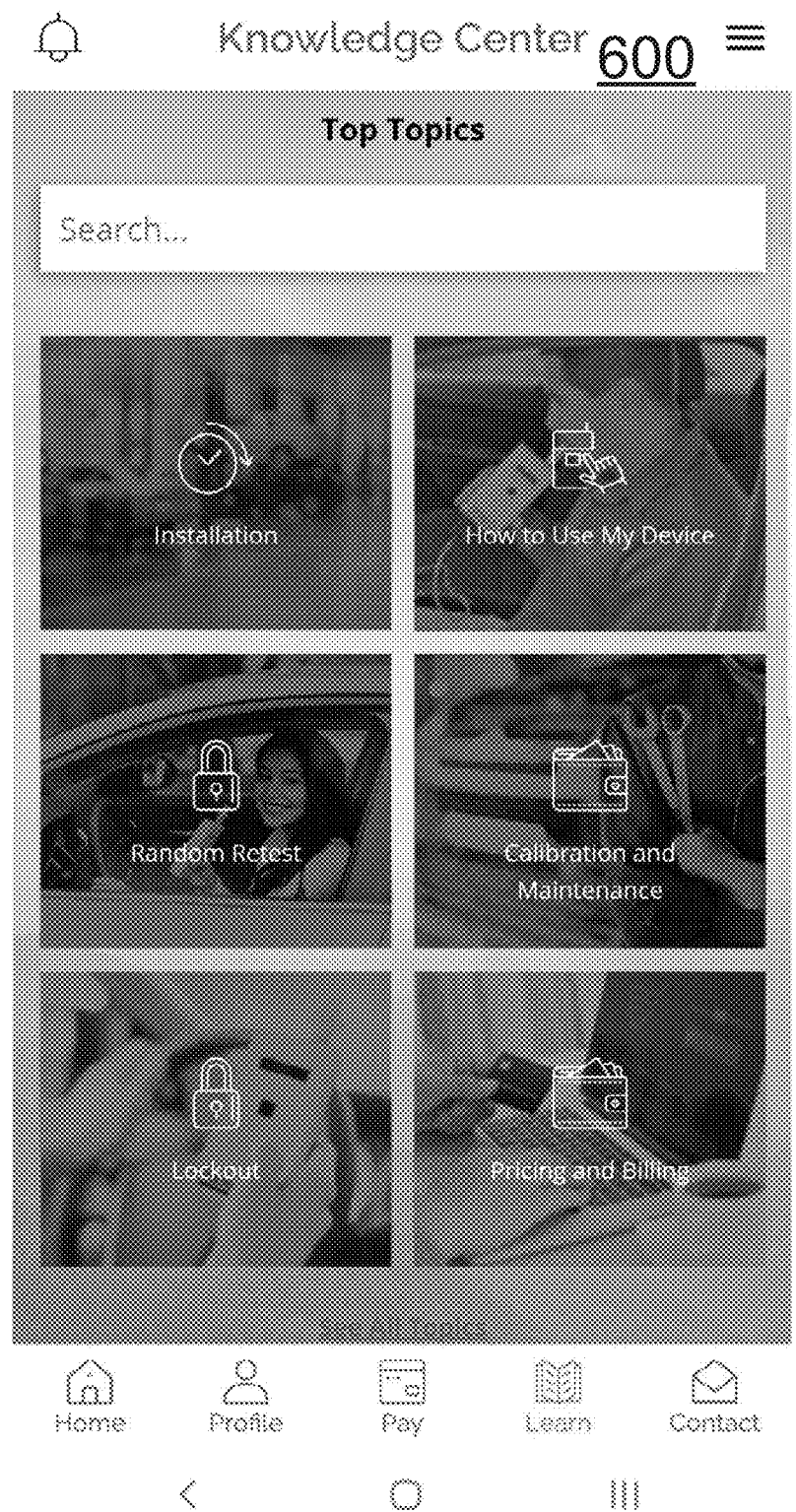
FIG. 6 is a knowledge center page of the mobile application of FIG. 1 in accordance with various embodiments herein.

FIG. 6 is a knowledge center page 600 of the mobile application of FIG. 1 in accordance with various embodiments, depicting alternative arrangements for aspects described with reference to embodiments described herein.

Figure 7:
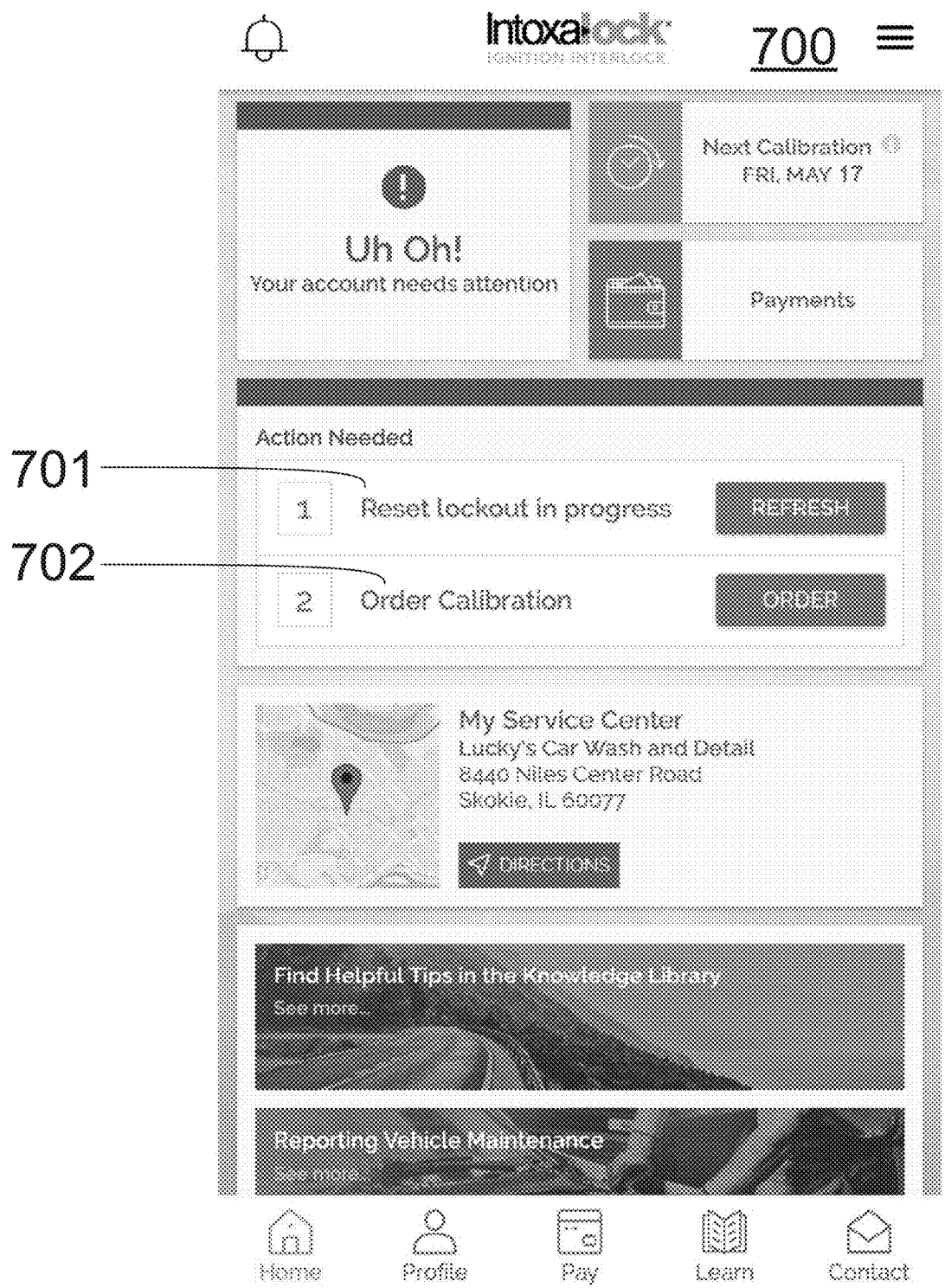
FIG. 7 is another home page of the mobile application of FIG. 1 in accordance with various embodiments herein.

FIG. 7 is another home page 700 of the mobile application of FIG. 1 in accordance with various embodiments. A user can be provided with a notification, "Reset lockout in progress." A user can be provided with reset lockout in progress option 701, and a communication option to order a re-calibration appointment 702 with the re-calibration service facility.

Figure 8:
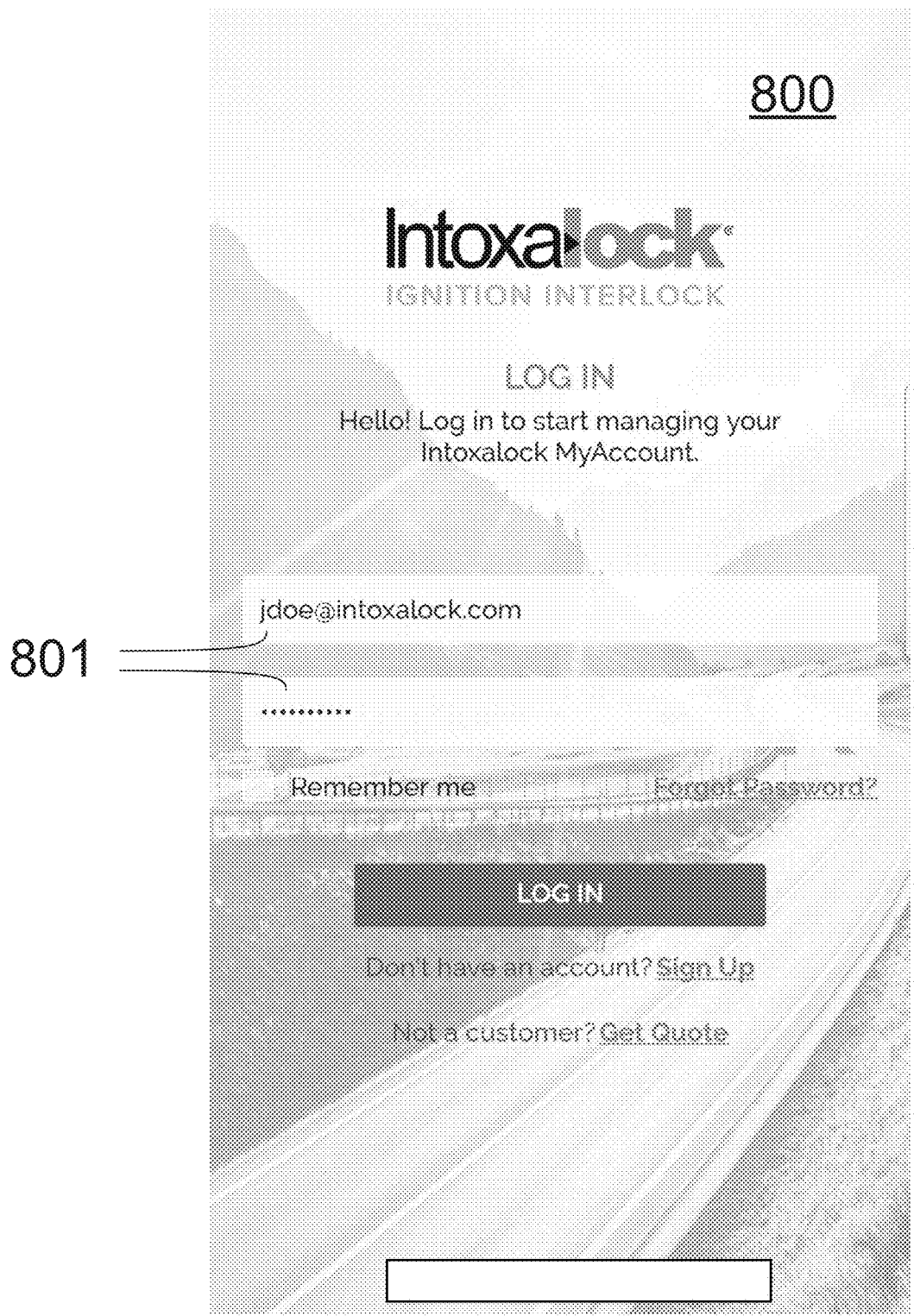
FIG. 8 is a login page of the mobile application of FIG. 1 in accordance with various embodiments herein.

FIG. 8 is a login page 800 of the mobile application of FIG. 1 in accordance with various embodiments herein, in accordance with personal account details 801 associated with an IID user.

Figure 9:
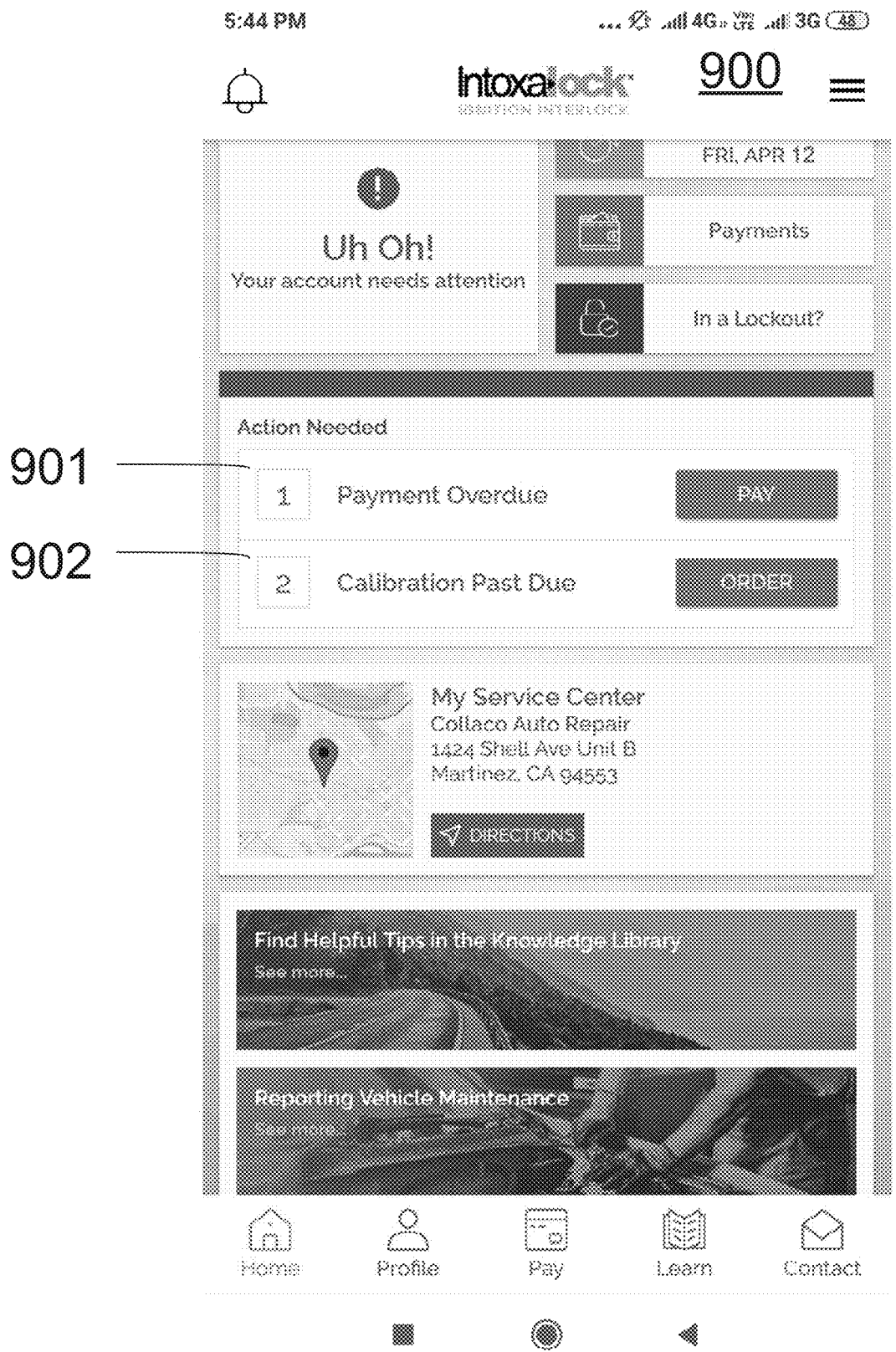
FIG. 9 is another home page of the mobile application of FIG. 1 in accordance with various embodiments herein.

FIG. 9 is another home page 900 of the mobile application of FIG. 1 in accordance with various embodiments herein. Push notifications relating to payment overdue condition 901 and calibration past due condition 902 can be displayed to a user upon such conditions being triggered for a given user account.

Figure 10:
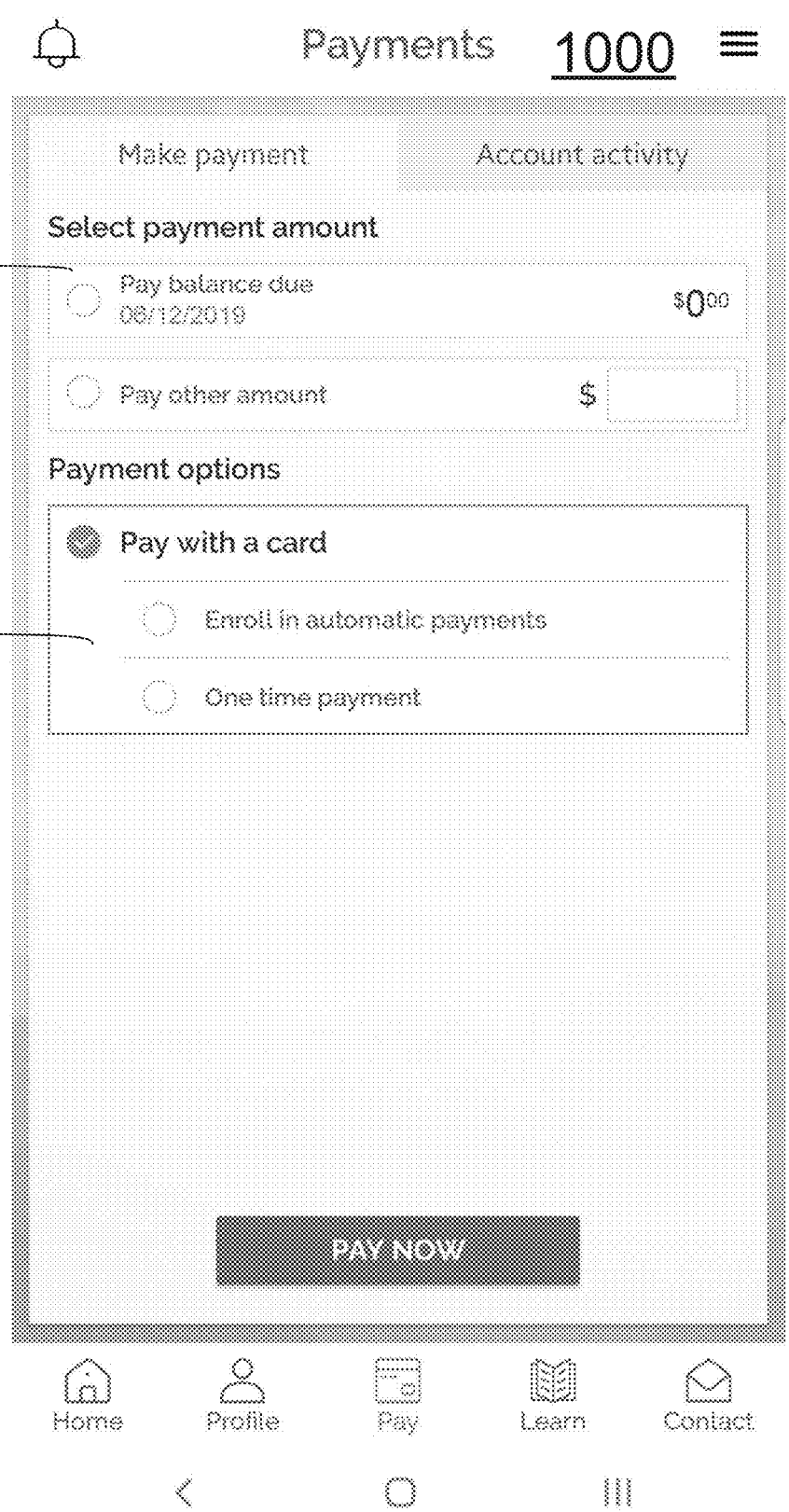
FIG. 10 is a payment page of the mobile application of FIG. 1 in accordance with various embodiments herein.

FIG. 10 is a payment page 1000 of the mobile application of FIG. 1 in accordance with various embodiments herein. Payment operations can include an option for payment of a balance due 1001 and also options for selecting method of payment 1002.

Figure 11:
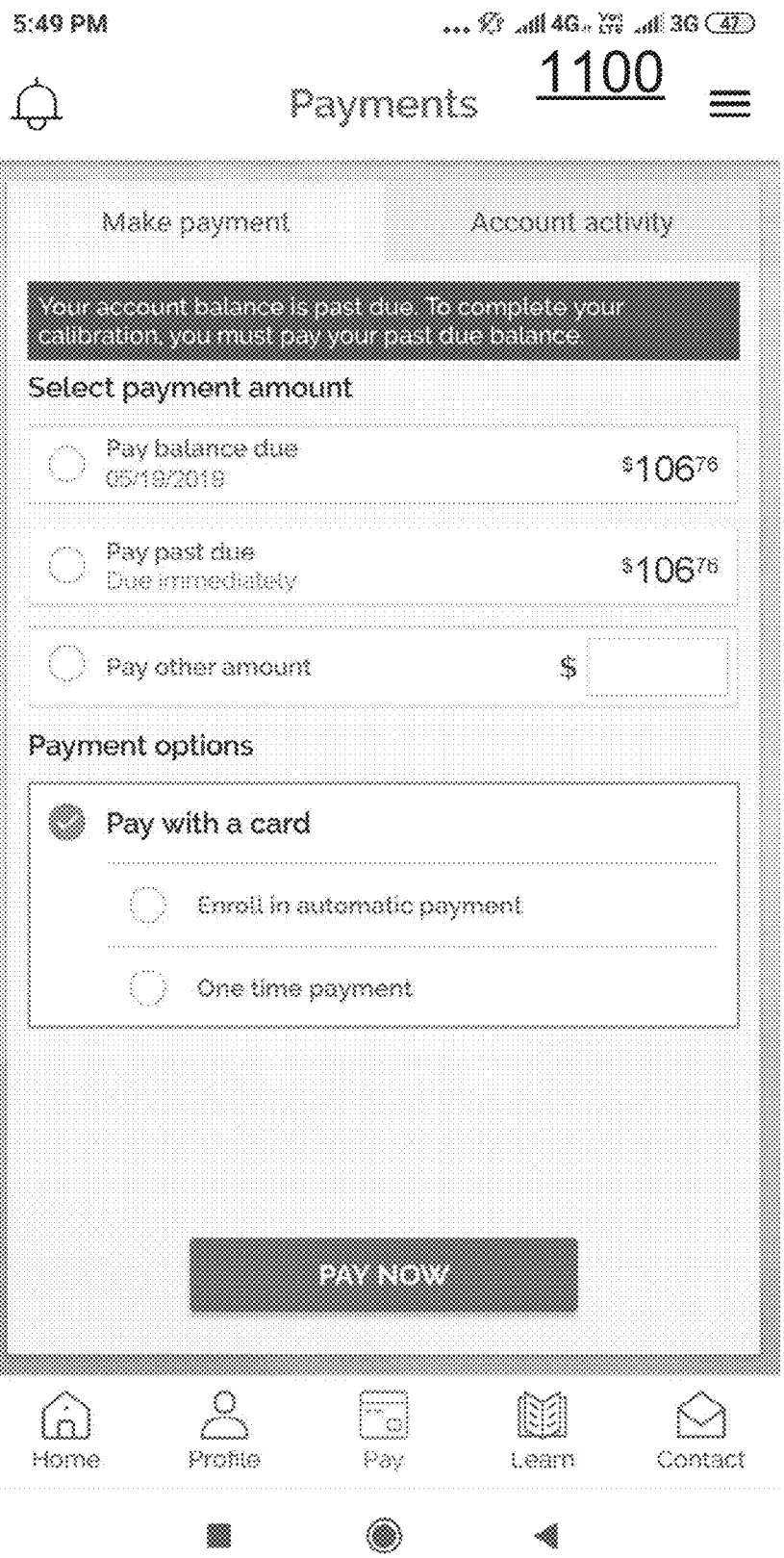
FIG. 11 is another payment page of the mobile application of FIG. 1, showing payment amount and method selection options in accordance with various embodiments herein.

FIG. 11 is an alternative payment page 1100 of the mobile application of FIG. 1, showing payment amount and method selection options in accordance with various embodiments herein.

Figure 12:
FIG. 12 is another payment page of the mobile application of FIG. 1, showing transaction history in accordance with various embodiments herein.

FIG. 12 is another payment page 1200 of the mobile application of FIG. 1, showing transaction history aspects 1201-1206 in accordance with various embodiments.

Figure 13:
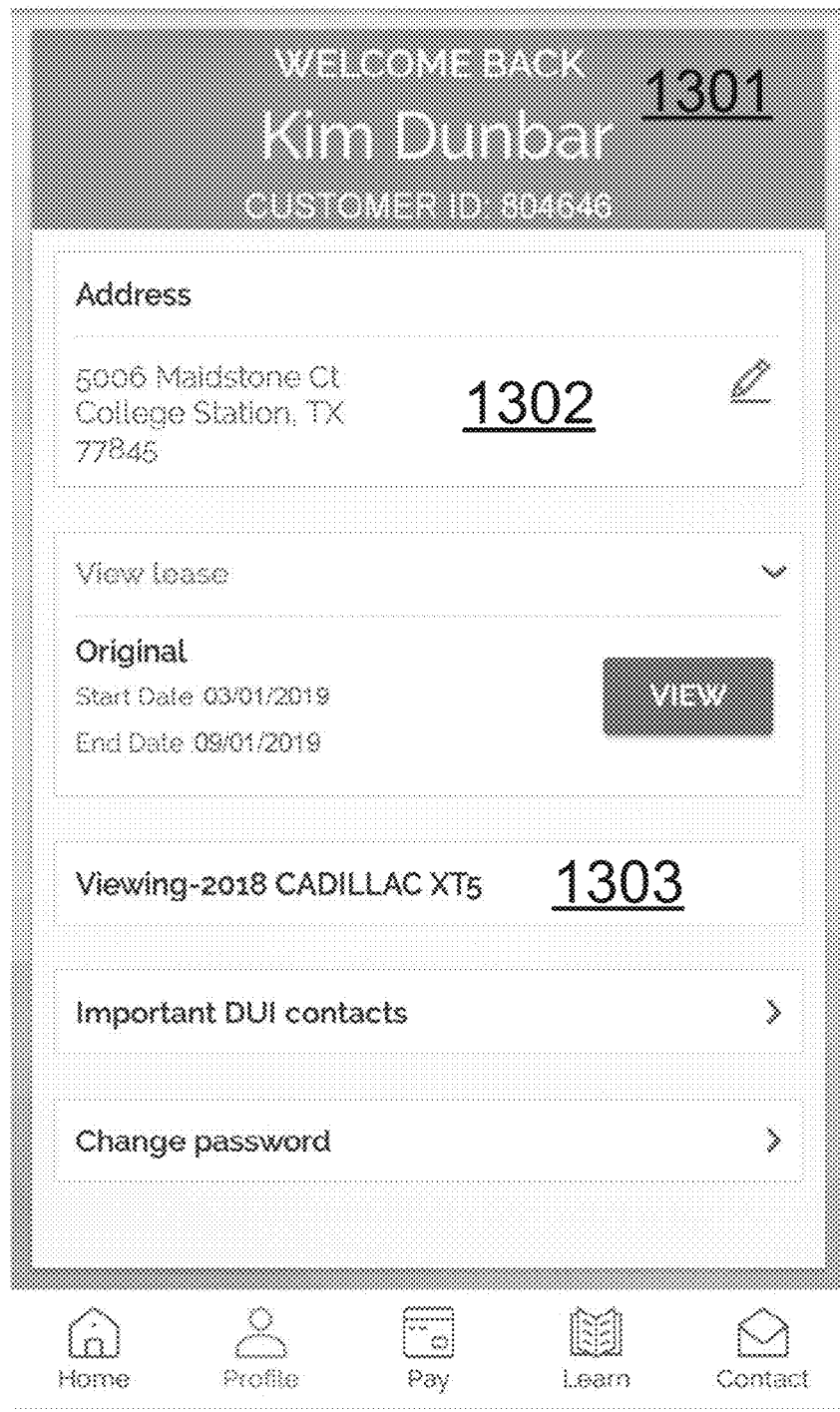
FIG. 13 is a My Account page of the mobile application of FIG. 1 in accordance with various embodiments herein.

FIG. 13 is a My Account page 1300 of the mobile application of FIG. 1 in accordance with various embodiments, in which a vehicle and IID are registered by the IID provider in relation with a given user account.

Figure 14:
FIG. 14 is a View Lease page of the mobile application of FIG. 1 in accordance with various embodiments herein.

FIG. 14 is a View Lease page 1400 of the mobile application of FIG. 1 in accordance with various embodiments, providing transaction details of a lease entered into between the IID user and the IID service provider, in one embodiment.

Figure 15:
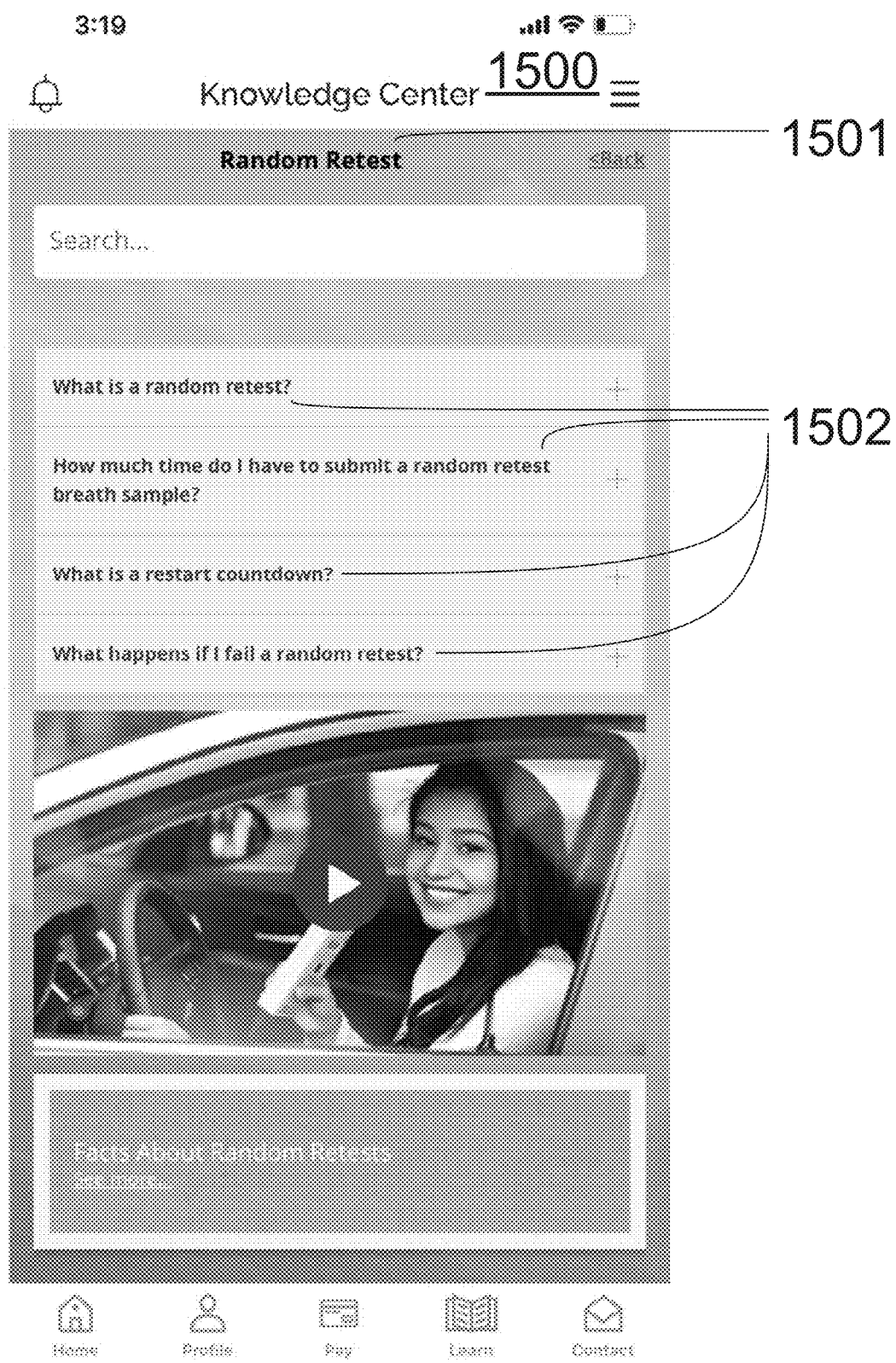
FIG. 15 is a knowledge center page of the mobile application of FIG. 1, showing options for getting more information about the particular topic of rolling retests in accordance with various embodiments herein.

FIG. 15 is a knowledge center page 1500 of the mobile application of FIG. 1, showing options for providing more detailed information about the particular topic of random or rolling retests 1501, 1502 in accordance with various embodiments herein.

Quick Indicator Functionality and Sources of Data

Data from the data logs about the vehicle and the intoxication interlock device are other types of data that could be provided to the user via the mobile application. Push notifications could be used to provide this data.

Data such as mentioned herein can be used to push customized notification to users. If data indicates a problems with the device operation, possible effort to tamper with the device, or both, the user might be informed, "We have identified that your device may need servicing. Please schedule an appointment," or a similar message. The user may also be informed of a low vehicle battery status, cold temperatures, information about the health of the vehicle, or other information.

Reset Lockout Functionality for IID Devices that Include Cell Phone Communicators If a user provides a sample that exceeds the allowable breath alcohol limit, then the device will trigger a requirement that the device be serviced by the interlock company. The user can use the mobile application to request a lockout reset to satisfy this request. The user will need to pay a lockout fee, and can be presented with the option to pay that fee via the mobile application. When a lockout reset has been requested, the home screen, such as shown in FIG. 7, can display the status of the lockout reset request.

In order to accomplish the lockout reset, a central server of the interlock company communicates with the IID using the cell phone communicator of the IID to change the status of the IID so that it is not in a lockout status. As a result, the user can provide another sample to attempt to start the vehicle.

Reset Lockout Functionality for IID Devices without Cell Phone Communicators

Many IIDs lack a cell phone communicator and the interlock company does not have an ability to communicate with the IID to get it out of a lockout status. A customer with such a device can still request a lockout reset via the mobile application. The customer can pay for the lockout fee using the mobile application. This request will initiate a work order in the interlock company's system. That work order will be provided to a service center. The service center can be a service center assigned to the particular customer or a service center close to the customer's location as automatically determined using the mobile application. The mobile application will then instruct the client to bring the device to the service center. The mobile application can queue up the phone number and phone functionality for the customer to dial to schedule an appointment.

Notifications about the Reset Lockout Functionality

The mobile application can provide push notifications to the phone on which the mobile application, via the mobile application, via text message, and/or via email. Examples of notification content include the following text or text with a similar meaning:

1. You are in lockout. Press the button to request a reset.
2. Your lockout reset request has been received in our queue.
3. Reset lockout in progress.
4. Your device has been reset.
5. You may call customer service to inquire about your reset request. (This message may be displayed for users of IIDs without cell phone communicators, or for IIDs with cell phone communicators if the lockout is not cleared after 15 minutes.)
6. You are in lockout. Press the button to request a reset. Then you will need to call the service center to initiate a work order.
7. You have requested a lockout set. We have created a work order for your IID. The next step is to bring your device to the service center.
8. Press below to call the service center to schedule an appointment.

Customer Dashboard

A customer dashboard can be included as a part of a home page. A dashboard can indicate the customer's aggregated status. A red action card or indicator can be provided when the customer needs to take action. A green action card or indicator can be shown when the client is current on bills and no action is currently needed for normal operation. If a red status is shown, the customer may be required to address the red status before the customer can move forward with a calibration process. The customer dashboard can also show the date of or time remaining before a required next calibration process, the date of or time remaining before the device must be taken in for service, or both. The timeframes of calibration requirements and service requirements vary by state, and can be complex to track. The mobile application provides an easy and automated way for this information to be presented to the customer.

Payment Center

A payment page may be provided as a part of the mobile application and can provide an interface to a secure terminal payment card industry (PCI) compliant system for receiving the customer's payment. The customer can select amount of payment, method of payment, and frequency of payment using the mobile application. In some embodiments, these options can be selected within the mobile application without connecting to the secure terminal.

Service Center

A service center is assigned to a client and that assignment is known to the interlock company and to the mobile application. The mobile application can interact with a map web service, such as Google Map, to easily and automatically provide directions to the service center. If a servicing requirement is within a specified number of days, such as 10 days, the mobile application can provide a notification and option to call the service center to make an appointment.

Knowledge Center

The content of the knowledge center can be dynamically populated based on tenure of the customer. Examples of information that may be available in the knowledge center include how to use a particular IID, how to calibrate an IID, how to troubleshoot an IID, state regulations related to IIDs, counseling centers for alcohol and other addiction, attorneys specializing in legal issues related to driving while intoxicated, how do I avoid a lockout in my state, billing information, lease information, opt in and opt out fees, educational videos, installation notifications, and other topics.

Warm-Up/Power Save Functionality

The mobile application could provide the user with information about the power status of the Intoxication Interlock Device (IID). IID's typically draw some power from the vehicle battery to operate an internal device heater. This heater reduces warm-up times when the user is ready to provide a sample. However, it may be desirable for the IID to go into a lower power mode state or a sleep state during very cold weather. In addition or alternatively, it may be desirable for the IID to go into a lower power mode state or a sleep state when the vehicle battery charge is low. If the IID goes into a lower power state or a sleep state, the mobile application could inform the user of that change. The mobile application could also warn the user if the vehicle's battery charge is low. The mobile application could warn the user if the weather forecast is for very low temperatures.

Figure 16:
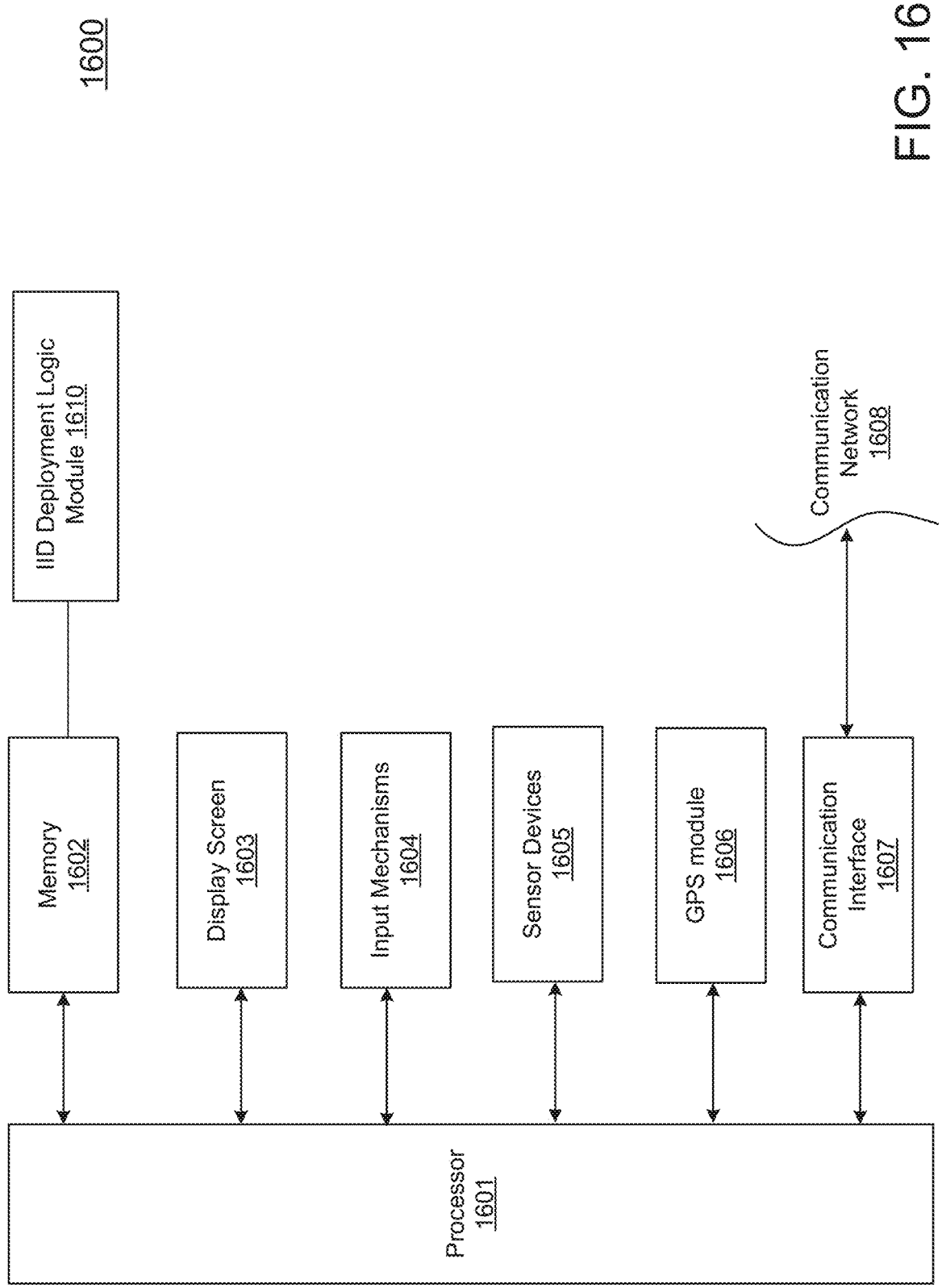
FIG. 16 illustrates an example architecture of a computing and communication device for deploying ignition interlock device functionality.

FIG. 16 illustrates an example architecture of a computing and communication mobile device 1600 for deploying IID functionality. In one embodiment, mobile device 1600 may correspond to, for example, a cellular or other wireless computing and communication tablet or mobile handheld device that is capable of telephony, messaging, and/or data computing services. Mobile device 1600 may include processor 1601, memory 1602, display screen 1603, input mechanisms 1604 such as resistive- or capacitance-based input mechanisms or software-implemented touchscreen input functionality. Mobile device 1600 may also include capability for detecting and communicatively accessing wireless communication signals, including but not limited to any of Bluetooth, Wi-Fi, RFID, and GPS signals, and incorporate communication interface 1607 for communicatively coupling to communication network 1608, such as by sending and receiving cellular data over data channels and voice channels.

IID deployment logic module 1610, in one embodiment can be embodied in a downloaded mobile application stored in memory 1602 of mobile device 1600 may include processor-executable instructions stored in RAM, for deploying IID functionality in conjunction with user interface renderings at display screen 1603 of mobile device 1600. The term mobile application as used herein refers to a downloaded mobile application stored in memory 1602 that incorporates IID deployment logic module 1610.

One or more embodiments described herein provide that methods, techniques, and actions performed by a computing device are performed programmatically, or as a computer-implemented method. Programmatically, as used herein, means through the use of code or computer-executable instructions. These instructions can be stored in one or more memory resources of the computing device. A programmatically performed step may or may not be automatic.

One or more embodiments described herein can be implemented using programmatic modules, engines, or components. Furthermore, one or more embodiments described herein may be implemented through the use of instructions that are executable by one or more processors. A programmatic module, engine, or component can include a program, a sub-routine, a portion of a program, or a software component or a hardware component capable of performing one or more stated tasks or functions. As used herein, a module or component can exist on a hardware component independently of other modules or components. Alternatively, a module or component can be a shared element or process of other modules, programs or machines.

Some embodiments described herein can generally require the use of computing devices, including processor and memory resources. For example, one or more embodiments described herein may be implemented, in whole or in part, on computing devices such as servers, desktop computers, mobile devices including cellular or smartphones, wearable devices, tablet devices and laptop computing devices. Memory, processing, and network resources may all be used in connection with the establishment, use, or performance of any embodiment described herein, including with the performance of any method or with the implementation of any system.

FIG. 17 illustrates, in an example embodiment, a method 1700 of deploying ignition interlock device functionality.

Examples of method steps described herein are related to the use of mobile device 1600 used in deploying IID functionality. According to one embodiment, the techniques are performed the processor 1601 executing one or more sequences of software logic instructions that constitute IID deployment logic module 1610 of computing device 1600. In embodiments, IID deployment logic module 1610 may include the one or more sequences of processor-executable instructions. Such instructions may be read into memory 1602 from machine-readable medium, such as memory storage devices. Executing the instructions of IID deployment logic module 1610 stored in memory 1602 causes processor 1601 to perform the process steps described herein. It is contemplated that, in some implementations, portions of executable instructions constituting IID deployment logic module 1610 may be hosted at a server device accessible to computing device 1600. In alternative implementations, at least some hard-wired circuitry may be used in place of, or in combination with, the software logic instructions to implement examples described herein. Thus, the examples described herein are not limited to any particular combination of hardware circuitry and software instructions.

At step 1710, upon processor 1601 executing instructions of IID deployment logic module 1610, receiving data in authentication of a user account associated with the IID.

At step 1720, upon processor 1601 executing instructions of IID deployment logic module 1610, rendering a user interface at the mobile computing device, the user interface including indication of a status of the user account associated with the IID.

At step 1730, upon processor 1601 executing instructions of IID deployment logic module 1610, receiving a selection of a user action responsive to the status of the user account associated with the IID.

In some embodiments, the rendering comprises indicating the status as a lockout in progress.

In some aspects the method further comprises soliciting, in response to the lockout in progress, at least one of a lockout reset and initiation of a communication session with an IID service provider associated with the user account.

In some embodiments, the rendering comprises indicating the status as IID re-calibration required and displaying at least a re-calibration due date.

In some aspects the method further comprises rendering identification of a re-calibration service facility determined as one of: geographically proximate to a registered location associated with the user account, and geographically proximate to a current location of the IID.

In some aspects the method further comprises soliciting, within the user interface, a user response to the status indicated as IID re-calibration required.

In some embodiments, the user response relates to scheduling a re-calibration service appointment with the re-calibration service facility.

Some aspects further comprise transmitting, to at least one of an IID service provider associated with the user account and the re-calibration service facility, a request for the re-calibration service appointment.

In embodiments, the rendering comprises indicating the status as a lowered power state of the IID in response to at least one of: an ambient temperature below a threshold temperature value, and a vehicle battery charge level below a predetermined threshold level.

In some embodiments, the rendering comprises a home page associated with the user account, the home page displaying a set of user selectable options, the selectable options including at least an operational payment facility, an IID lease agreement record, an IID user manual, and a set of communication options enabled to initiate a communication session in real time.

It should be noted that, as used in this specification and the appended claims, the singular forms "a," "an," and "the" encompass plural referents unless the content clearly dictates otherwise. It should also be noted that the term "or" is generally employed in its sense including "and/or" unless the content clearly dictates otherwise. Furthermore, as used in the disclosure herein and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged.

It is contemplated for embodiments described herein to extend to individual elements and concepts described herein, independently of other concepts, ideas or system, as well as for embodiments to include combinations of elements recited anywhere in this application. Although embodiments are described in detail herein with reference to the accompanying drawings, it is contemplated that the disclosure herein is not limited to only such literal embodiments. As such, many modifications including variations in sequence of the method steps in conjunction with varying combinations of user interface features disclosed herein will be apparent to practitioners skilled in this art. Accordingly, it is intended that the scope of the invention be defined by the following claims and their equivalents. Furthermore, it is contemplated that a particular feature described either individually or as part of an embodiment can be combined with other individually described features, or parts of other embodiments. Thus, the absence of describing combinations, including user interface manifestation of such, do not preclude the inventor from claiming rights to such combinations.

What is claimed is:

1. A method, executed in a processor of a mobile computing device, of deploying an ignition interlock device (IID), the method comprising:
   rendering a user interface at the mobile computing device, the user interface including an indication of a status of the user account associated with the IID, wherein the user interface comprises a warning indicating that the user is at risk of having an extension in an IID compliance program, and an indication of the status as a lowered power state of the IID in response to at least one of: an ambient temperature below a threshold temperature value, and a vehicle battery charge level below a predetermined threshold level; and
   receiving a selection of a user action responsive to the status of the user account associated with the IID.

2. The method of claim 1, wherein the user interface comprises guidance for reinstating a user's vehicle operation license privileges.

3. The method of claim 1, wherein the user interface comprises an extension risk score, wherein the extension risk score is indicative of a likelihood of the user having an extension in an IID compliance program.

4. The method of claim 3, wherein the extension risk score is based on user behavior and data from other IID users.

5. The method of claim 3, wherein the extension risk score can be one of a high extension risk score indicating a high likelihood of the user having an extension, a medium extension risk score indicating a medium likelihood of the user having an extension, and a low extension risk score indicating a low likelihood of the user having an extension.

6. The method of claim 1, further comprising collecting data from logs about the IID, collecting data from a vehicle associated with the IID, and generating a notification to the user based on the collected data.

7. The method of claim 6, wherein the collected data indicates any of problems with operation of the IID or possible efforts to tamper with the IID, and wherein the notification comprises a message indicating that the IID may need servicing.

8. The method of claim 1, wherein the user interface comprises and a recalibration due date for the IID, and a rendering identification of a re-calibration service facility determined as one of: geographically proximate to a registered location associated with the user account, and geographically proximate to a current location of the IID.

9. The method of claim 1, wherein the user interface comprises a date of or a time remaining before a required next calibration process, and an option for the user to order a re-calibration appointment.

10. The method of claim 1, wherein the user interface comprises a date of or a time remaining before a required next calibration process, and instructions for the user to address the warning prior ordering a re-calibration appointment.

11. A method, executed in a processor of a mobile computing device, of deploying an ignition interlock device (IID), the method comprising:
   rendering a user interface at the mobile computing device, the user interface including an indication of a status of the user account associated with the IID, wherein the user interface comprises an extension risk score, wherein the extension risk score is indicative of a likelihood of the user having an extension in an IID compliance program, and an indication of the status as a lowered power state of the IID in response to an ambient temperature below a threshold temperature value; and receiving a selection of a user action responsive to the status of the user account associated with the IID.

12. The method of claim 11, wherein the user interface comprises guidance for reinstating a user's vehicle operation license privileges.

13. The method of claim 12, wherein the guidance is based on data collected by the mobile computing device.

14. The method of claim 12, wherein the guidance is based on data comprising any of device data, environmental conditions, state rules regarding IID usage, and historical records of the user's behavior.

15. The method of claim 11, wherein the user interface comprises a warning indicating that the user is at risk of having an extension in an IID compliance program.

16. The method of claim 11, wherein the extension risk score can be one of a high extension risk score indicating a high likelihood of the user having an extension, a medium extension risk score indicating a medium likelihood of the user having an extension, and a low extension risk score indicating a low likelihood of the user having an extension.

17. The method of claim 11 further comprising collecting data from logs about the IID, collecting data from a vehicle associated with the IID, and generating a notification to the user based on the collected data.

18. The method of claim 17, wherein the collected data indicates any of problems with operation of the IID or possible efforts to tamper with the IID, and wherein the notification comprises a message indicating that the IID may need servicing.

19. A computing system for deploying ignition interlock device (IID) functionality, the computing system comprising:
   a processor;
   a memory storing a set of instructions, the instructions when executed in the processor causing operations comprising:
   rendering a user interface at the computing system, the user interface including indication of a compliance status of the user account associated with the IID, wherein the user interface comprises a warning indicating that the user is at risk of having an extension in an IID compliance program, and an indication of the status as a lowered power state of the IID in response to a vehicle battery charge level below a predetermined threshold level; and
   receiving a selection of a user action responsive to the status of the user account associated with the IID.

20. The system of claim 19, wherein the user interface comprises an extension risk score, wherein the extension risk score is indicative of a likelihood of the user having an extension in an IID compliance program.

* * * * *